United States Patent [19]
Greathouse

[11] Patent Number: 5,936,163
[45] Date of Patent: Aug. 10, 1999

[54] PORTABLE HIGH TEMPERATURE ULTRASONIC TESTING (UT) PIEZO PROBE WITH COOLING APPARATUS

[76] Inventor: John D. Greathouse, 611 Brook Hollow Dr., Conroe, Tex. 77385

[21] Appl. No.: 09/076,985

[22] Filed: May 13, 1998

[51] Int. Cl.⁶ .............................. G01N 24/00; G01H 11/00
[52] U.S. Cl. .................................................. 73/644; 73/649
[58] Field of Search ........................................ 73/570–672

[56] References Cited

U.S. PATENT DOCUMENTS

| | | | |
|---|---|---|---|
| 3,555,297 | 1/1971 | Pierson | 310/325 |
| 3,979,946 | 9/1976 | Cipywnyk | 73/635 |
| 4,509,360 | 4/1985 | Erwin et al. | 73/644 |
| 4,526,038 | 7/1985 | Box et al. | 73/644 |
| 4,567,770 | 2/1986 | Rumbold et al. | 73/644 |
| 4,887,460 | 12/1989 | Khosropour | 73/579 |
| 5,195,373 | 3/1993 | Light et al. | 73/644 |
| 5,450,753 | 9/1995 | Maynor et al. | 73/644 |
| 5,546,809 | 8/1996 | Cotton | 73/644 |
| 5,585,565 | 12/1996 | Glascock et al. | 73/644 |
| 5,708,209 | 1/1998 | Stiffler et al. | 73/644 |
| 5,821,418 | 1/1999 | Dubois | 73/644 |

Primary Examiner—Hezron Williams
Assistant Examiner—Chad Soliz
Attorney, Agent, or Firm—Gunn & Associates, P.C.

[57] ABSTRACT

The invention provides protection of the heat sensitive piezo ultrasonic transducer by controlling the environmental temperature in which the transducer operates. As temperature rises in the cooling chamber coolant may be circulated in order to draw off excessive heat. This allows non-destructive testing of high temperature reactors and steam piping without the need for system shutdown.

12 Claims, 2 Drawing Sheets

PORTABLE HIGH TEMPERATURE ULTRASONIC TESTING (UT) PIEZO PROBE WITH COOLING APPARATUS

TECHNICAL FIELD OF THE INVENTION

The present invention relates to an ultrasonic piezo transducer/probe and the cooling chamber (heat sink) that will allow liquid coolant to be circulated around or through the piezo transducer/probe in high temperature applications, for the purpose of preventing damage to the piezo/probe at elevated temperatures.

BACKGROUND OF THE INVENTION

Piezo ultrasound devises provide ultrasonic emissions to measure the thickness of materials, particularly metal. High temperature causes these electronic devises to become erratic and unreliable.

At present it is generally necessary to protect the piezo probe by using delay lines or delay blocks, which are devices that allow the ultrasonic probe to be in contact with the elevated temperature surface material for a longer period of time.

In practice, the probes are not held on the elevated temperature surface for more than a few seconds before they heat up and become erratic or are damaged. Since these are hand held devices, the operator cannot hold his hand steady and in place long enough for an accurate reading to be made.

On repeated contacts on the elevated temperature surface, the piezo probe becomes so over heated that its readings are not correct. Therefore, this method of measuring on a elevated temperature surface is not reliable or safe.

SUMMARY OF THE INVENTION

The present invention protects the unltrasonic testing (UT) piezo transducer/probe from high temperature failure and allows the operator to properly operate the instrument. The piezo transducer/probe is protected by a layer of high temperature elastomer or plastic. The piezo transducer/probe is immersed or surrounded in a coolant which is contained in a cooling chamber (heat sink) containing liquid or gas coolant, which may be circulated by a pumping system.

The piezo probe is maintained at a temperature not exceeding that of the cooling chamber (heat sink) liquid. The heat imposed on the probe is substantially reduced to a level consistent with the working temperature design of the instrument. The invention by design allows the operator's hands to be positioned away from the heat source.

BRIEF DESCRIPTION OF THE DRAWINGS

For a more complete understanding of the present invention, and for the further details and advantages thereof, reference is now made to the following detailed description taken in conjunction with accompanying drawings in which.

DETAILED DESCRIPTION OF A PREFERRED EMBODIMENT

Figure 1:
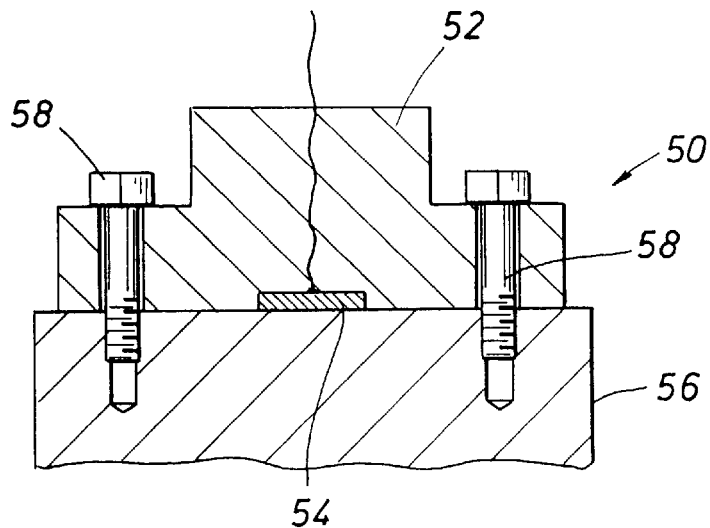
FIG. 1 is a sectional view of a prior art piezo probe with a delay line/delay block attached.

FIG. 1 depicts a known piezo probe (50). This probe comprises primarily a transducer component (52) with active piezoelectric element (54). The transducer component (52) is held in abutting contact with a delay block (56) as by screws (58). As the probe (50) is brought in contact with an object surface for non-destructive testing (NDT), the delay block provides a temperature gradient so that the probe can remain on the surface a bit longer.

Figure 2:
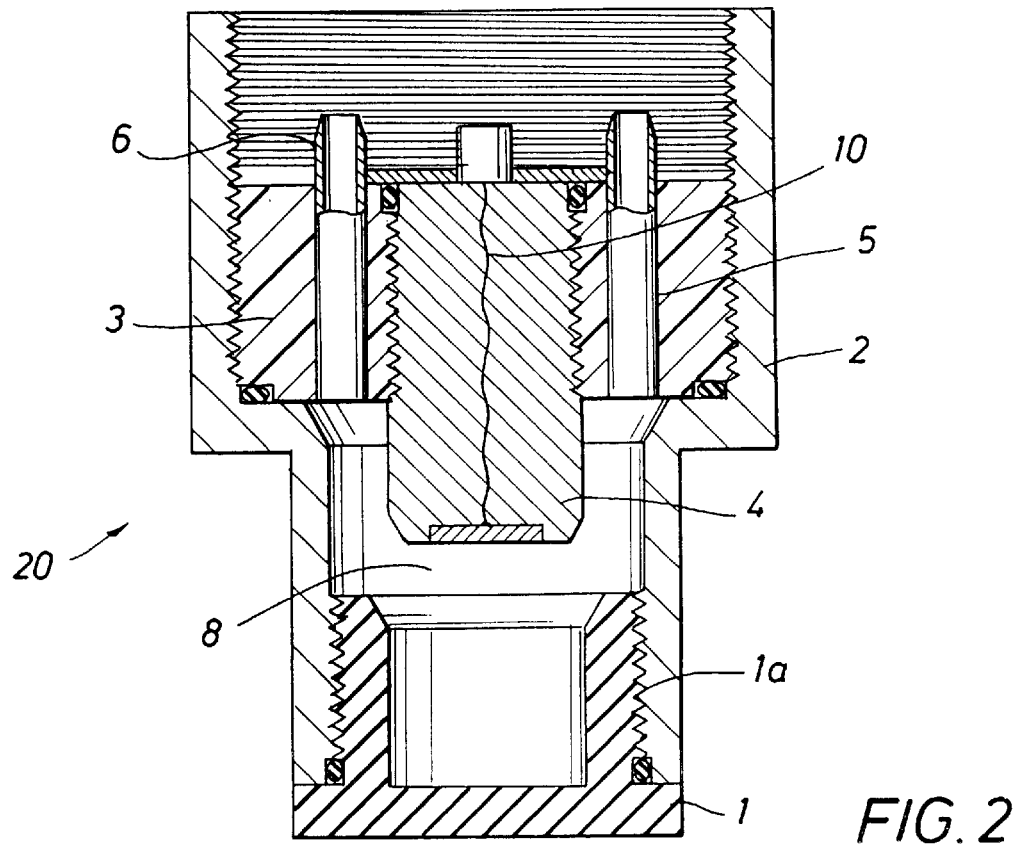
FIG. 2 is a longitudinal sectional view of a piezo probe encased in polymer and protected by a cooling chamber (heat sink) of coolant and a high temperature elastomer contact plate or plastic tip that is actually in contact with the heated surface.
Figures 2A, 3:
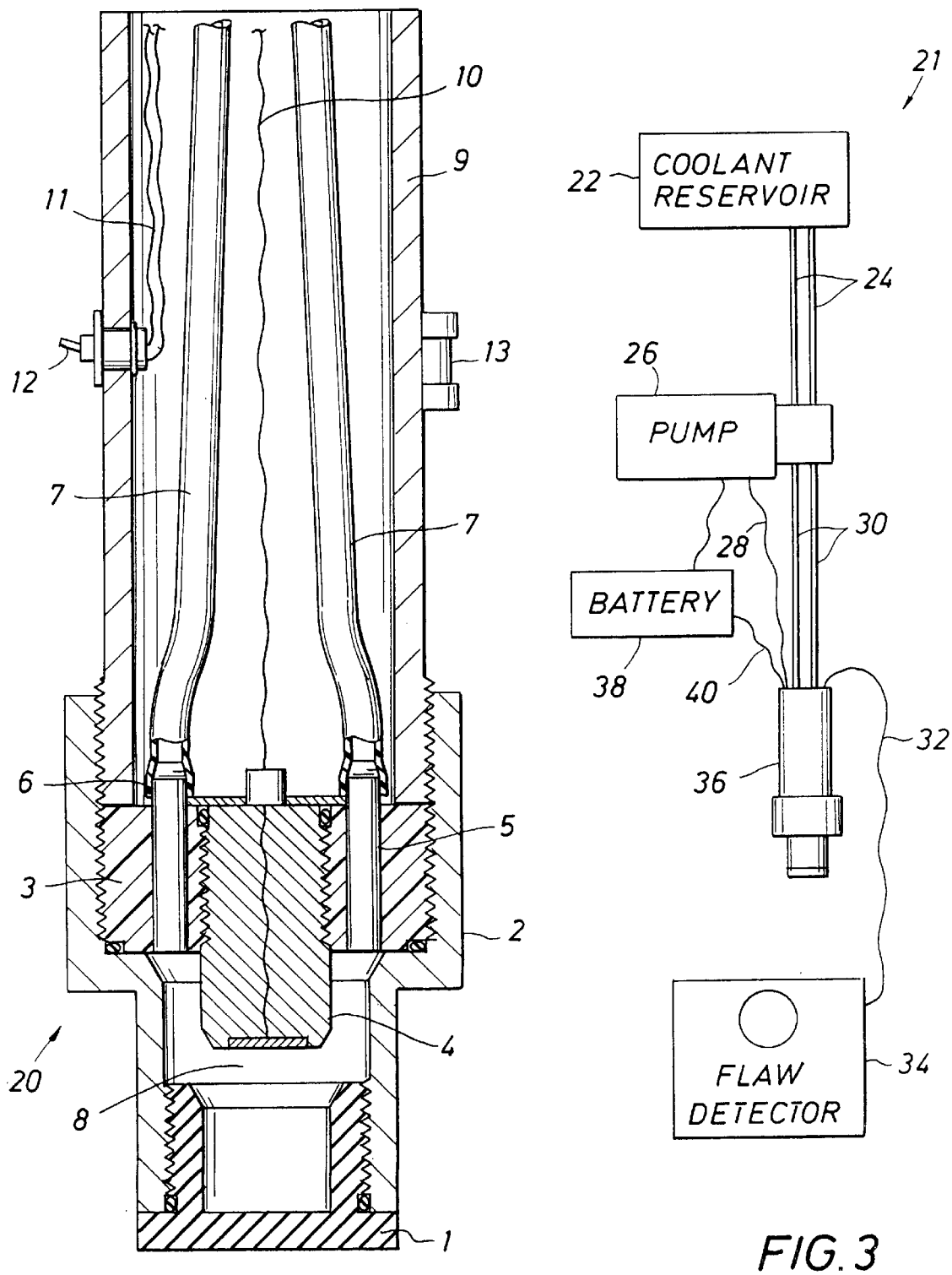
FIG. 2A is a longitudinal sectional view of the assembled invention.
FIG. 3 is a schematic drawing of the complete cooling system, including the coolant reservoir, coolant tubing, coolant pump, and control system.

FIG. 2A illustrates an improved high temperature ultrasonic (UT) cooling chamber probe (20) manufactured from elastomer bar stock. Other embodiments allow it be molded or extruded material from various plastics or metallic materials. A contact plate, or tip (1) is made from a high temperature elastomer such as but not limited to PTFE. It may be screwed or otherwise connected into a body (2) as by threads (1a) and is sacrificial. An internal adapter (3) is manufactured from any olefin or thermosetting machinable plastic or metal. A piezo transducer (4) can either be machined into or screwed or otherwise connected with the adapter (3), depending on the type of transducer (4) employed.

In this embodiment, coolant taps or holes (5) are drilled into the adapter (3) with connections (6) to cooling tubes (7). Coolant from a reservoir source, as shown in FIG. 3, is circulated through the cooling chamber (heat sink) (8). A tubular handle (9) is incorporated. The handle (9) also serves as a conduit to house the tubing (7) and wiring (10) and (11) coming out of the probe, shown in FIG. 2. A switch (12) controls a pump (26) to circulate the coolant.

The portable pump system shown in FIG. 3 is included as an embodiment of the invention. The design of the portable pumping system will vary and the drawing of FIG. 3 does not limit the invention to a particular design.

A bubble type level (13) is used to assist the operator in obtaining vertical alignment for the invention.

FIG. 3 depicts a pumping system (21) that circulates coolant through and around the piezo tube. The pumping system consists of a coolant reservoir (22) which holds coolant. Inlet and outlet tubing (24) goes to the coolant pump (26). Wiring (28) comes from the switch (12) to control the on/off of the pump (26). Coolant tubing (30) transports coolant in and out of the high temperature piezo probe cooling chamber (8). The system further includes (UT) lead wire (32) coming out of high temperature piezo probe (36) going to a (UT) flaw detector (34). A battery (38) powers the pump through wiring (40).

I claim:

1. An ultrasonic probe for performing non-destructive testing of a hot, solid material, the probe comprising:
   a. a substantially cylindrical body defining a lower end and an upper end;
   b. a contact plate enclosing the lower end of the body, the contact plate adapted for abutting contact with the material under test;
   c. an internal adapter within the upper end of the body, the contact plate and the internal adapter defining a volume with the body;
   d. inlet and outlet coolant penetrations through the internal adapter for circulating coolant through the volume; and
   e. a piezo transducer in the internal adapter in a spaced apart relationship from the contact plate so that a portion of the volume lies between the piezo transducer and the contact plate.

2. The probe of claim 1, further comprising a source of coolant coupled to the inlet.

3. The probe of claim 2, further comprising a receiver coupled to the outlet.

4. The probe of claim 3, further comprising a pump to pump coolant from the source into the inlet and out the outlet so that coolant flows between the piezo transducer and the contact plate.

5. The probe of claim 4, further comprising a tubular handle joined to and extending from the body.

6. The probe of claim 5, further comprising an electrical switch on the handle and electrically coupled to the pump to control the actuation of the pump.

7. The probe of claim 5, further comprising level indicating means on the handle.

8. The probe of claim 1, wherein the contact plate is formed of a high temperature elastomer.

9. The probe of claim 1, wherein the probe is portable.

10. A method of inducing an ultrasonic signal onto a high temperature solid surface with an ultrasonic probe, comprising the steps of:

a. placing a contact plate in contact with the surface, wherein said contact plate encloses a lower end of a cylindrical body;

b. inducing an ultrasonic signal from a signal source, wherein said signal source is within an internal adapter enclosing an upper end of said cylindrical body; and c. circulating a coolant through a volume defined by said contact plate and said adapter with said cylindrical body, such that a portion of the volume lies between said signal source and said contact plate.

11. The method of claim 10, wherein the contact plate and the signal source are mounted to a common body and the body is coupled to a handle extending from the body.

12. The method of claim 11, further comprising the step of verifying the orientation of the probe with a level detector on the handle.

* * * * *